United States Patent [19]
Edwardson

[11] 4,453,918
[45] Jun. 12, 1984

[54] ARTICULATOR FOR USE IN MAKING DENTURES OF PARTS THEREOF

[75] Inventor: Svante R. Edwardson, Solna, Sweden

[73] Assignee: AB Dentatus, Hagersten, Sweden

[21] Appl. No.: 422,477

[22] Filed: Sep. 23, 1982

[51] Int. Cl.³ .................................................. A61C 11/00
[52] U.S. Cl. ........................................................ 433/55
[58] Field of Search .............................. 435/55, 57, 59

[56] References Cited
U.S. PATENT DOCUMENTS 2,603,869  7/1952  Bjorklund .............................. 433/57

Primary Examiner—Robert Peshock
Attorney, Agent, or Firm—Young & Thompson

[57] ABSTRACT

An articulator for use in making dentures or parts thereof comprises two principal members that are movably interconnected by means of a condylar mechanism. Each of two condylar track members of said condylar mechanism is pivotable around two different axes for allowing different attitudes of the condylar track to be set, and there is a lock for locking each of said condylar track members in a desired attitude. This lock comprises for each condylar track member a locking mechanism enabling simultaneous locking against movement around the two axes, as well as enabling simultaneous unlocking for allowing movement around either or both of these axes.

9 Claims, 6 Drawing Figures

ARTICULATOR FOR USE IN MAKING DENTURES OF PARTS THEREOF

The present invention relates to an articulator, for use in making dentures or parts thereof, comprising a lower and an upper principal member which are interconnected by means of a condylar mechanism that allows relative movement between said principal members, the lower principal member being provided with two condylar track members incorporated in said condylar mechanism, each of said track members having a condylar track for a condylar ball, each of said track members being pivotable around a horizontal pitch axis for varying condylar track inclination and also being pivotable around a vertical yaw axis for varying the condylar track yaw angle, locking means being provided for locking the condylar track members in a desired attitude.

Numerous types of such articulators for simulating a patient's bite and jaw movements are found on the market. One such semi-adjustable articulator is Dentatus Articulator Type ARH, manufactured by AB Dentatus, Hägersten, Sweden. In said articulator each condylar track member is mounted in a circular holder in which it can be pivoted and locked in various positions for testing various condylar track inclinations. For adjusting the condylar track member around a vertical yaw axis, e.g. resetting the Bennett angle, a separate locking mechanism has to be manipulated.

There are also articulators where the Bennett angle can be adjusted, but where the condylar track inclination can only be changed by replacing the condylar track members with other condylar track members where the inclination of the condylar track is different. In order to obtain flexibility it is thus necessary to have a set of different condylar track members. Handling thus becomes complicated.

To be found on the market are also articulators where no adjustment at all of the condylar track is possible. Such articulators are generally called average type articulators, e.g. they are preset to certain average values for the condylar track inclination and the Bennett angle.

The object of the invention is to provide an articulator that is simple, easy to handle, but yet has good adjustability.

Said object is achieved, according to the invention, by providing an articulator where said locking means comprises for each condylar track member a locking mechanism enabling simultaneous locking against movement around both said pitch axis and said yaw axis, as well as enabling simultaneous unlocking for allowing movement around either or both of said axes.

In this way only one locking mechanism is needed for controlling both the condylar track inclination setting and the Bennett angle setting.

An especially compact design is obtained when said locking mechanism comprises an anchoring means movably anchored in the condylar track member for allowing the track member to pivot around said pitch axis, said locking mechanism also comprising tightening means cooperating with said anchoring means, for tightening the condylar track member against a support means incorporated in said lower principal member.

The following is a description, by way of example only, of an embodiment of the invention, reference being made to the accompanying drawings, in which.

Figure 1:
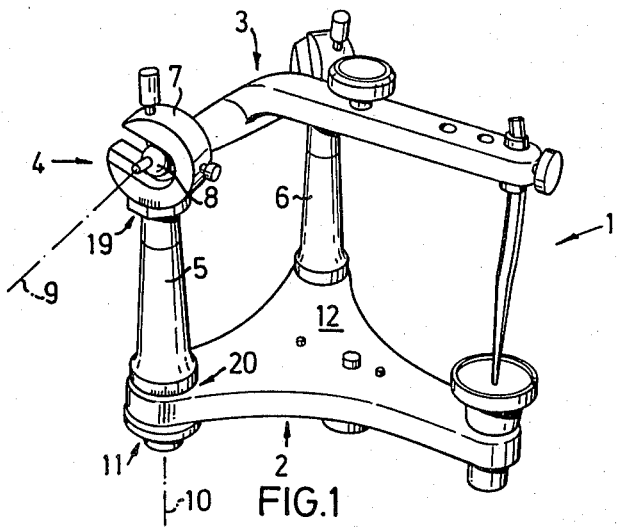
FIG. 1 shows a perspective view of an articulator according to the invention.

As can be seen from FIG. 1, an articulator 1 according to the invention comprises a lower principal member 2 and an upper principal member 3. The principal members 2 and 3 are interconnected by a condylar mechanism 4 that allows relative movement between said principal members 2 and 3 in order to simulate the movements of the jaw joint. The lower principal member 2 is provided with two support means 5 and 6, each supporting a condylar track member 7 which holds a condylar ball 8 incorporated in the upper principal member 3.

Each condylar track member 7 is pivotable around a horizontal pitch axis 9, for varying the condylar track inclination, and around a vertical yaw axis 10, for varying the Bennett angle, i.e. the toe-in, of the condylar track. At each support means 5 and 6 there is provided a locking means, generally indicated by the reference numeral 11 at the support means 5, for locking the condylar track member 7 and thus the condylar track in a desired attitude. In the lower principal member 2 there is provided a base member 12 carrying the two support means 5 and 6, which are each pivotable around a yaw axis 10 relative to the base member.

Figure 3:
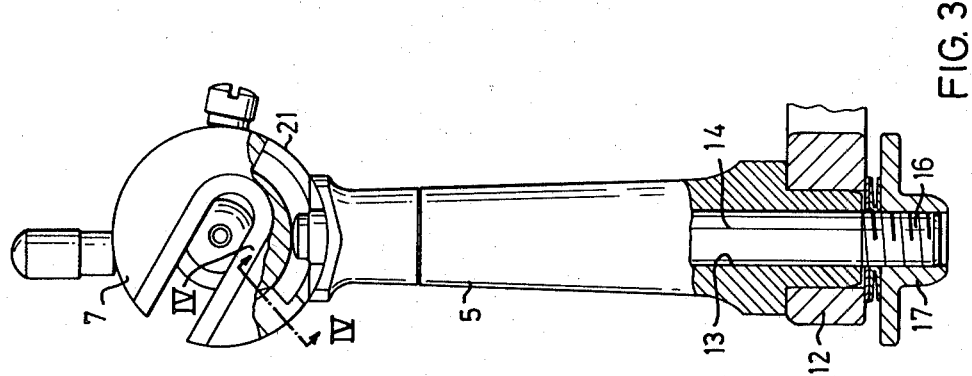
FIG. 3 shows, partly in section, a side view of the portion shown in FIG. 2.
Figure 2:
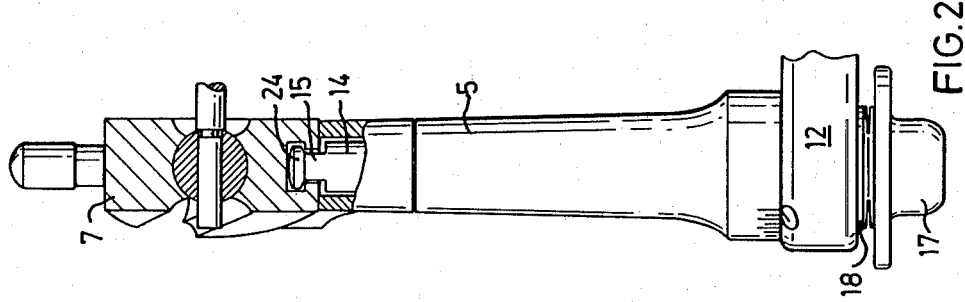
FIG. 2 shows, partly in section, a portion of the articulator in FIG. 1.

As can be seen from FIGS. 2 and 3 there is provided in a longitudinal bore 13 in the support means 5 an elongate anchoring means 14, the upper end 15 of which is in engagement with the condylar track member 7, and the lower end 16 of which is in threaded engagement with a tightening means 17 that also constitutes a stand for the lower principal member 12. Between the base member 12 and the tightening means 17 there is provided at least one spacer element 18.

By tightening the tightening means 17, the anchoring means 14 pulls down the condylar track member 7 against the support means 5 which in turn is pulled down against the base member 12, thereby locking the condylar track member 7 in a certain attitude. Index means 19 are provided on the condylar track member 7 and on the support means 5 for indicating the condylar track inclination. Further index means 20 are provided on the support means 5 and on the base member 12 for indicating the Bennett angle of the condylar track.

In an alternative embodiment the support means 5 and 6 need not be mounted directly in the base member 12. Rather, there could be provided fixed posts in the base member 12 for holding the support means 5 and 6, which would then of course be shorter. This would also mean a different location of the index means 20.

Figure 4:
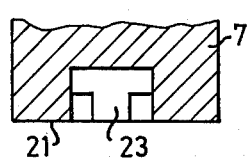
FIG. 4 shows a cross section along the line IV—IV in FIG. 3.
Figure 5:
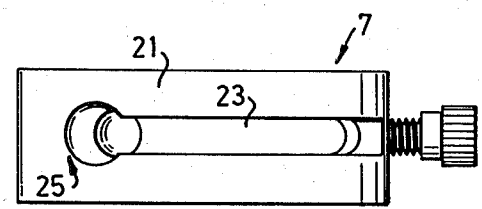
FIG. 5 shows a bottom view of a condylar track member.
Figure 6:
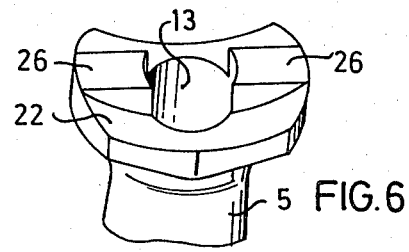
FIG. 6 shows a perspective view of the upper end of a support means.

Reference now being made to FIGS. 2-6, it will be seen that each condylar track member 7 is provided with a cylindrical support surface 21 for cooperation with a corresponding support surface 22 on the corresponding support means 5 or 6. In the condylar track member 7 there is provided a peripheral groove 23 for the upper end 15 of the anchoring means 14, said groove opening in said support surface 21. As seen in FIGS. 2 and 4 the groove 23 widens radially inwards to accommodate a head 24 on the upper end 15 of the anchoring means 14. Adjacent one of its ends the groove 23 has a wide portion 25 via which the upper end 15 of the anchoring means can be introduced into or removed from the groove 23.

Protruding from the support surface 22 on the support means 5 there are two guide means 26 intended to be located within the groove 23 for preventing the condylar track member 7 and the guide means 5 to pivot relative to each other around the yaw axis 10. Said two guide means 26 also limit, together with the groove 23, the angle the condylar track member can be pivoted around the pitch axis 9. The upper end 15 of the anchoring means 14 is slidable within the groove 23 when changing the condylar track inclination by pivoting the condylar track member 7 around the pitch axis 9.

When desiring to change the attitude of a condylar track member, the tightening means 17 of the locking means 11 is loosened so that the condylar track member 7 can be pivoted around either or both of the axes 9, 10. Having made the adjustments required, the tightening means 17 is again tightened, thus locking the condylar track member 7 in a set position.

What I claim is:

1. In an articulator, for use in making dentures or parts thereof, comprising a lower and an upper principal member which are interconnected by means of a condylar mechanism that allows relative movement between said principal members, the lower principal member being provided with two condylar track members incorporated in said condylar mechanism, each of said condylar track members having a condylar track for a condylar ball, each of said condylar track members being pivotable around a horizontal pitch axis for varying condylar track inclination and also being pivotable around a vertical yaw axis for varying the condylar track yaw angle, and locking means for locking the condylar track members in a desired attitude; the improvement in which said locking means comprises for each condylar track member a locking mechanism enabling simultaneous locking against movement around both said pitch axis and said yaw axis, as well as enabling simultaneous unlocking for allowing movement around either or both of said axes.

2. An articulator as claimed in claim 1, in which said locking mechanism comprises an anchoring means movably anchored in the condylar track member for allowing the track member to pivot around said pitch axis, said locking mechanism also comprising tightening means cooperating with said anchoring means, for tightening the condylar track member against a support means incorporated in said lower principal member.

3. An articulator as claimed in claim 2, in which the condylar track member and the support means are in mutual engagement for preventing mutual pivoting around said yaw axis.

4. An articulator as claimed in claim 3, in which the support means is mounted in a base member incorporated in said lower principal member, said support means being pivotable relative to said base member around said yaw axis, said anchoring means having a free end extending through said base member, said free end carrying said tightening means for tightening the support means against the base member while also tightening the condylar track member against the support means.

5. An articulator as claimed in claim 3, in which the condylar track member has a cylindrical support surface for cooperation with a corresponding surface on the support means, a peripheral groove in said condylar track member opening in said contact surface and widening radially inwards, said groove holding one end of said anchoring means slidably along the groove, and guide means on said support means cooperating with said groove for mutually interlocking said support means and the condylar track member around said yaw axis.

6. An articulator as claimed in claim 5, in which said groove has a wide portion adjacent one of its ends, said portion allowing one of said anchoring means to become engaged with or disengaged from the condylar track member.

7. An articulator as claimed in claim 4, in which said tightening means also constitutes a stand for the lower principal member.

8. An articulator as claimed in claim 2, and index means on said condylar track member and on said support means for indicating the condylar track inclination.

9. An articulator as claimed in claim 4, and index means on said support means and on said base member for indicating the yaw angle of the condylar track.

* * * * *